(12) United States Patent
Yun et al.

(10) Patent No.: US 11,497,829 B2
(45) Date of Patent: Nov. 15, 2022

(54) METHOD FOR MANUFACTURING SUPPORT FOR REGENERATING CORE-SHELL STRUCTURED HARD TISSUE AND SUPPORT FOR REGENERATING CORE-SHELL STRUCTURED HARD TISSUE MANUFACTURED THEREBY

(71) Applicant: KOREA INSTITUTE OF MACHINERY AND MATERIALS, Daejeon (KR)

(72) Inventors: Hui Suk Yun, Gyeongsangnam-do (KR); Naren Raja, Gyeongsangnam-do (KR); Jong Man Lee, Gyeongsangnamdo (KR)

(73) Assignee: KOREA INSTITUTE OF MACHINERY AND MATERIALS, Daejeon (KR)

( * ) Notice: Subject to any disclaimer, the term of this patent is extended or adjusted under 35 U.S.C. 154(b) by 405 days.

(21) Appl. No.: 15/137,378

(22) Filed: Apr. 25, 2016

(65) Prior Publication Data
US 2016/0250380 A1  Sep. 1, 2016

Related U.S. Application Data

(63) Continuation of application No. PCT/KR2014/002205, filed on Mar. 17, 2014.

(30) Foreign Application Priority Data

Nov. 8, 2013 (KR) .......................... 10-2013-0135202
Mar. 13, 2014 (KR) .......................... 10-2014-0029602

(51) Int. Cl.
| | | |
|---|---|---|
| *A61L 27/56* | (2006.01) | |
| *A61L 27/12* | (2006.01) | |
| *A61L 27/54* | (2006.01) | |
| *A61L 27/34* | (2006.01) | |
| *A61L 27/30* | (2006.01) | |
| *A61L 27/38* | (2006.01) | |
| *A61L 27/52* | (2006.01) | |

(52) U.S. Cl.
CPC ............ *A61L 27/12* (2013.01); *A61L 27/306* (2013.01); *A61L 27/34* (2013.01); *A61L 27/3847* (2013.01); *A61L 27/52* (2013.01); *A61L 27/54* (2013.01); *A61L 27/56* (2013.01); *A61L 2430/02* (2013.01)

(58) Field of Classification Search
None
See application file for complete search history.

(56) References Cited

U.S. PATENT DOCUMENTS

| 4,183,884 A * | 1/1980 | Wichterle | B29C 47/8895 |
| | | | 264/177.17 |
| 6,994,726 B2 * | 2/2006 | Lin | A61F 2/28 |
| | | | 264/250 |
| 8,709,452 B2 * | 4/2014 | Varghese | A61K 35/12 |
| | | | 424/400 |
| 2003/0090034 A1 * | 5/2003 | Mulhaupt | B29C 64/106 |
| | | | 264/255 |
| 2003/0236573 A1 * | 12/2003 | Evans | A61L 27/12 |
| | | | 623/23.58 |
| 2006/0036331 A1 * | 2/2006 | Lu | A61L 27/3891 |
| | | | 623/23.51 |
| 2007/0204929 A1 * | 9/2007 | Jarvenkyla | B29C 47/02 |
| | | | 138/145 |
| 2008/0103227 A1 * | 5/2008 | Yun | B29C 64/106 |
| | | | 523/105 |

(Continued)

FOREIGN PATENT DOCUMENTS

| KR | 1020040070346 A | 8/2004 |
| KR | 1020070028271 A | 3/2007 |
| KR | 100751504 B1 | 8/2007 |

(Continued)

OTHER PUBLICATIONS

English language Google-translate Machine translation of KR 10-2012-0139095, pp. 1-8 as provided. (Year: 2012).*

(Continued)

*Primary Examiner* — Tigabu Kassa
*Assistant Examiner* — Ivan A Greene
(74) *Attorney, Agent, or Firm* — Caesar Rivise, PC

(57) ABSTRACT

The present invention relates to a method for manufacturing a support for regenerating core-shell structured hard tissue and a support for regenerating core-shell structured hard tissue manufactured thereby, wherein the support may further comprise bio-functional materials, such as cells, in a core-shell structure. The method for manufacturing a support for regenerating core-shell structured hard tissue according to the present invention has an effect of manufacturing a support for regenerating core-shell structured hard tissue by a method by which a 3-dimensional structure is prepared by a layer manufacturing process through an extrusion container having a double nozzle. In addition, the support can be manufactured at room temperature, thereby having an effect of containing cells or various bio-functional materials. Furthermore, the support for regenerating core-shell structured hard tissue has a similar constitution to a bone component and thus has higher mechanical properties, and has an effect that the cells or various bio-functional materials are uniformly distributed throughout the entire 3-dimensional structure.

5 Claims, 10 Drawing Sheets

(56) References Cited

U.S. PATENT DOCUMENTS

| | | | | |
|---|---|---|---|---|
| 2012/0071884 | A1* | 3/2012 | Cooper | B01F 5/0685 606/93 |
| 2014/0186413 | A1* | 7/2014 | Kim | A61L 27/46 424/422 |

FOREIGN PATENT DOCUMENTS

| | | | |
|---|---|---|---|
| KR | 1020080017161 A | | 2/2008 |
| KR | 1020090046016 A | | 5/2009 |
| KR | 100941374 B1 | | 2/2010 |
| KR | 1020100013016 A | | 2/2010 |
| KR | 1020110099475 A | | 9/2011 |
| KR | 10-2012-0139095 | * | 12/2012 |
| KR | 1020120139095 | * | 12/2012 |
| KR | 1020120139095 A | | 12/2012 |
| KR | 101219646 B1 | | 1/2013 |

OTHER PUBLICATIONS

Zhao ("An injectable calcium phosphate-alginate hydrogel-umbilical cord mesenchymal stem cell paste for bone tissue engineering," Elsevier, Biomaterials, vol. 31, pp. 6502-6510 (Year: 2010).*

Machine (KIPO) translation of Korean priority document for Kim (US 2014/0186413), Korean Application No. 10-2012-0155310, pp. 1-21, as provided. (Year: 2012).*

Hollister, Scott J.; "Porous Scaffold Design For Tissue Engineering," 2005, Nature Publishing Group; Nature Materials, vol. 4, pp. 518-590. (Year: 2005).*

Luo et al.; "Well-ordered biphasic calcium phosphate scaffolds fabricated by multi-channel 3D plotting under mild conditions," Jun. 17, 2013, RSC Publishing; Journal of Materials Chemistry B, vol. 1, pp. 4088-4098. (Year: 2013).*

Moroni et al.; "Design of Biphasic Polymeric 3-Dimensional Fiber Deposited Scaffolds for Cartilage Tissue Engineering Applications," 2006, Mary Ann Liebert, Inc.; Tissue Engineering, vol. 13, No. 2, pp. 361-371. (Year: 2006).*

Jun et al., "Novel hydroxyapatite (HA) dual-scaffold with ultra-high porosity, high surface area, and compressive strength", J Mater Sci: Mater Med 18: 1071-1077 (2007).

Yun et al., "Design and preparation of bioactive glasses with hierarchical pore networks", Chem. Commun., 2139-2141 (2007).

Yun et al., "Three-dimensional mesoporous-giantporous inorganic/organic composite scaffolds for tissue engineering", Chemistry of Materials 19(26): 6363-6366 (2007).

International Search Report for PCT/KR2014/002205 dated Aug. 6, 2014.

* cited by examiner

[Figure 1]
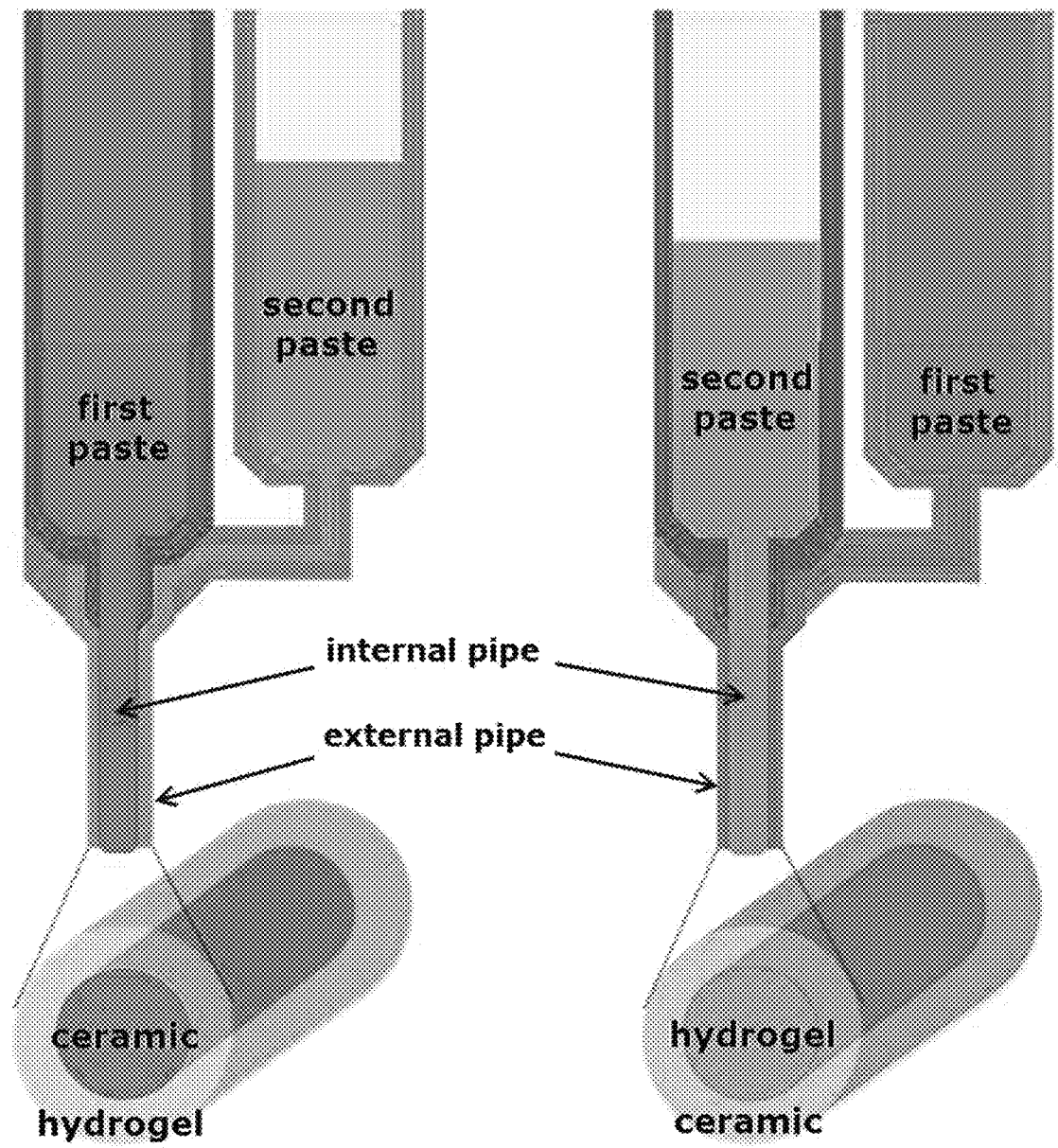

[Figure 2]
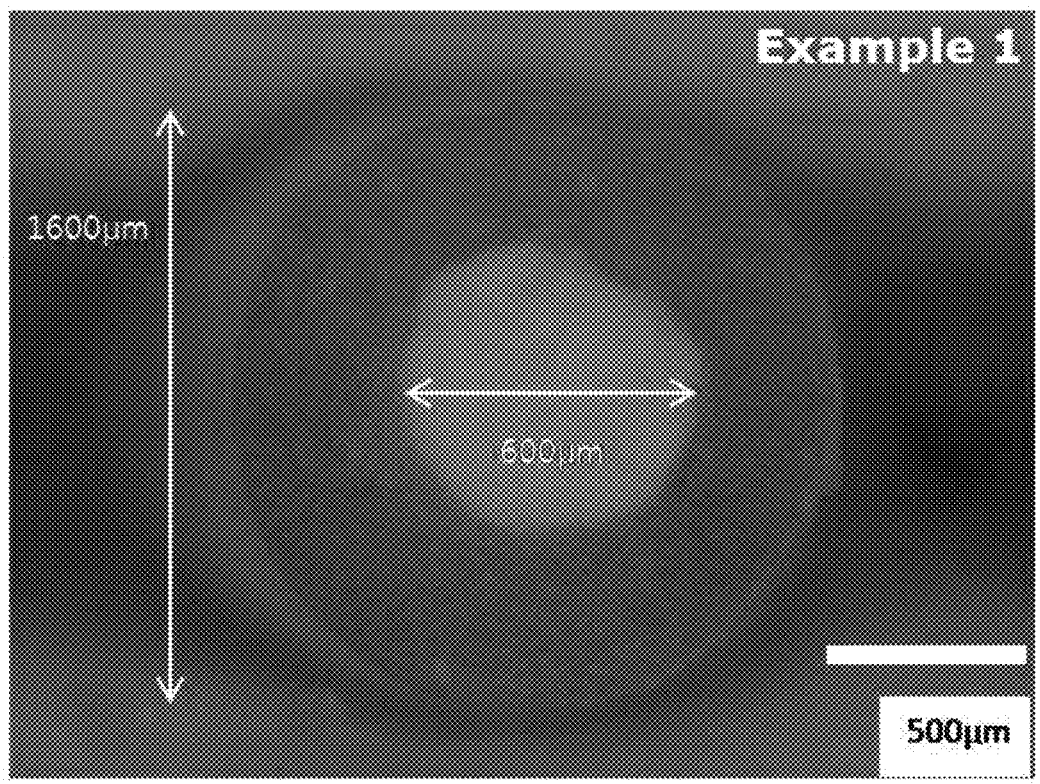
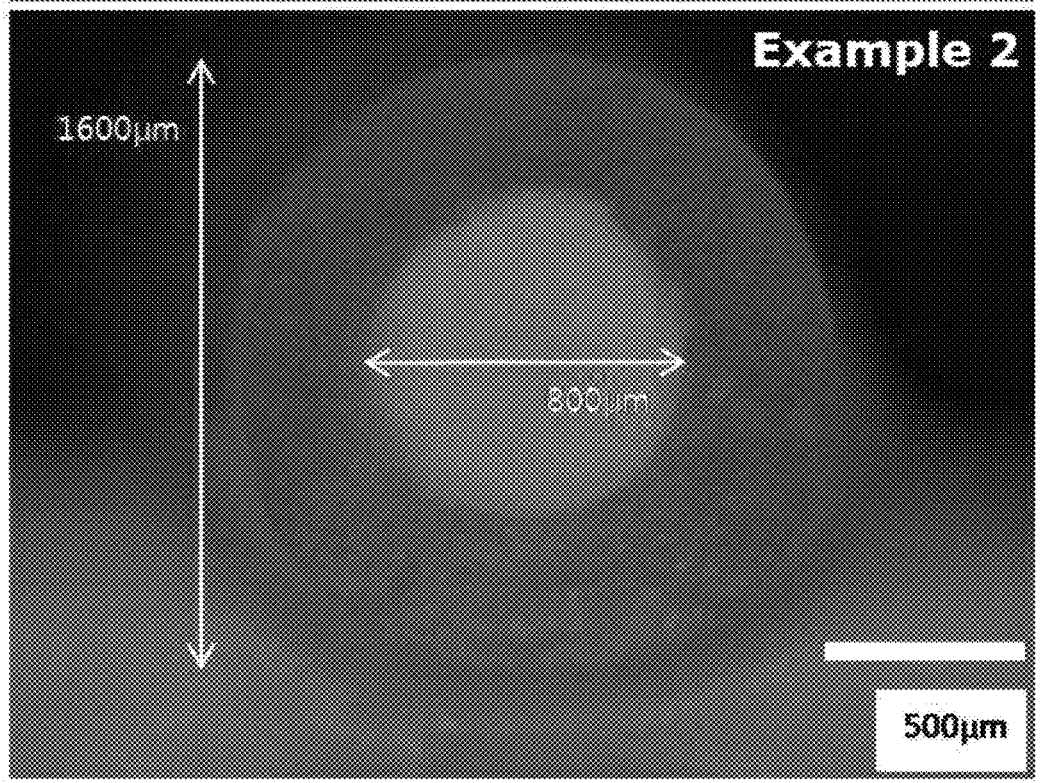

【Figure 3】
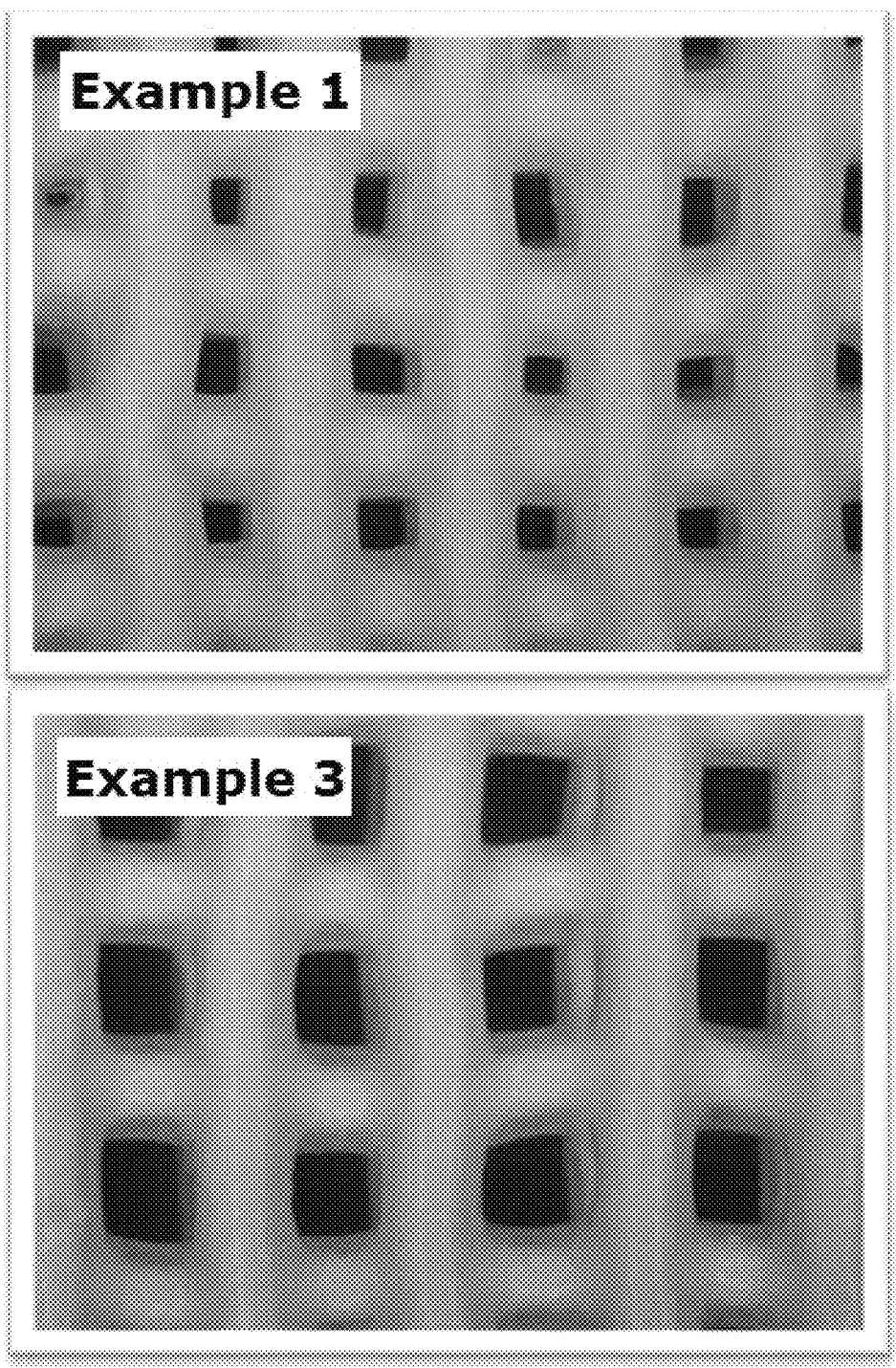

[Figure 4]
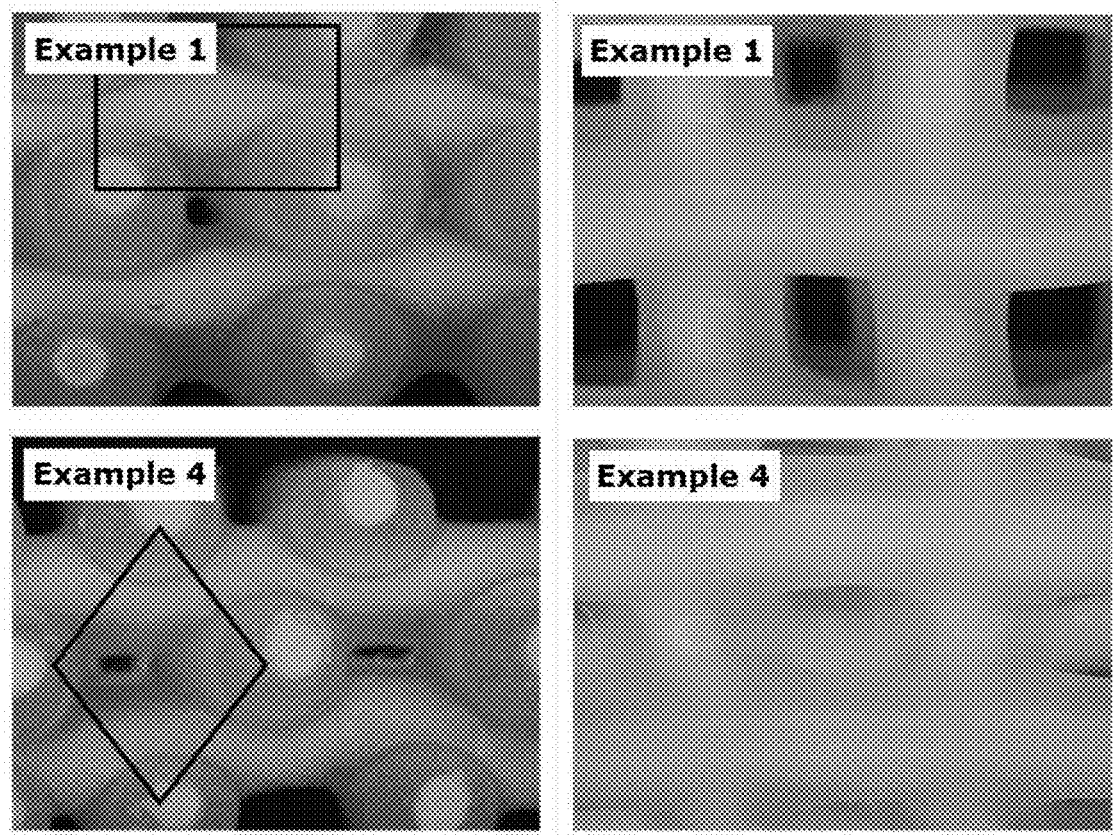

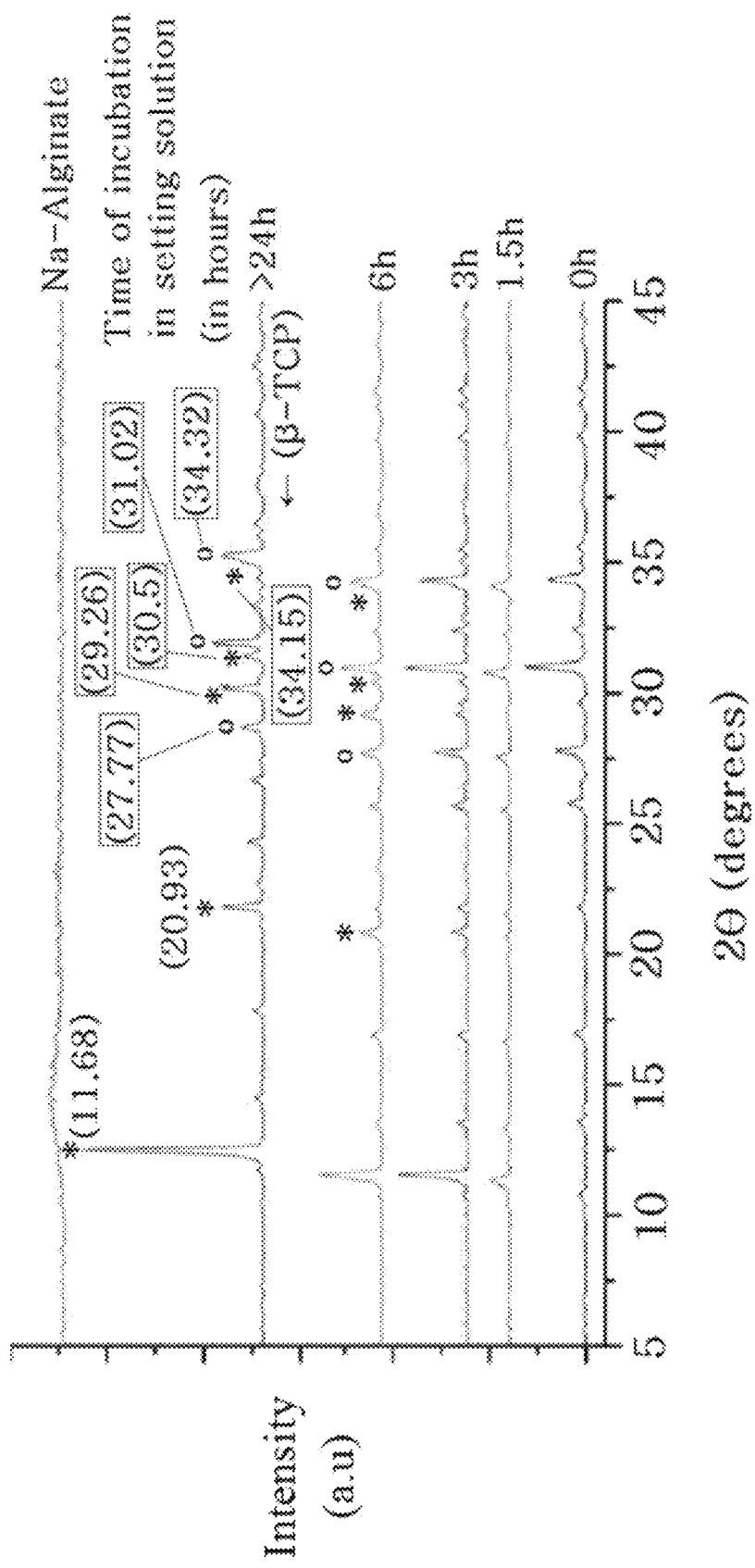

[Figure 6]
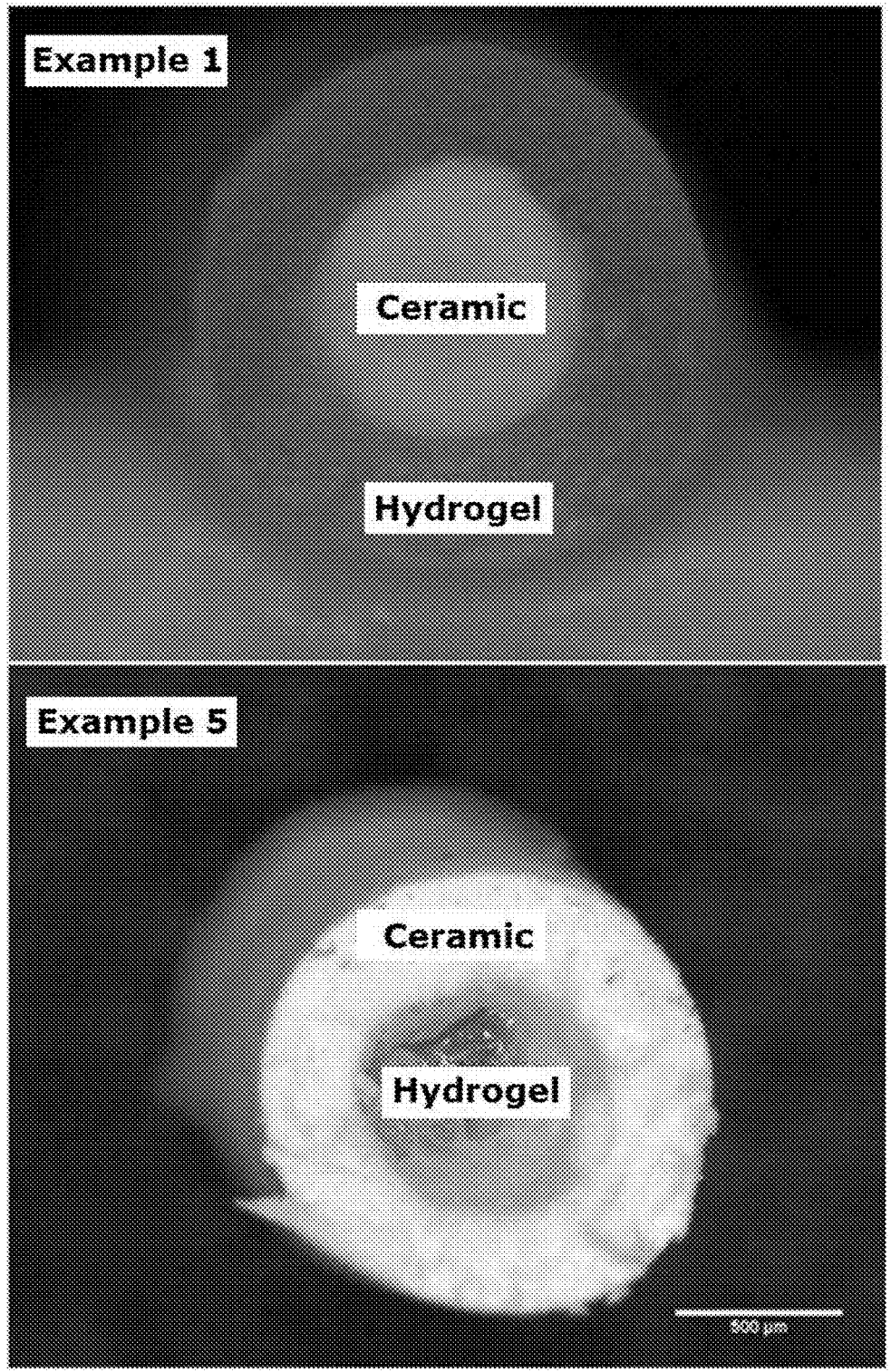

[Figure 7]
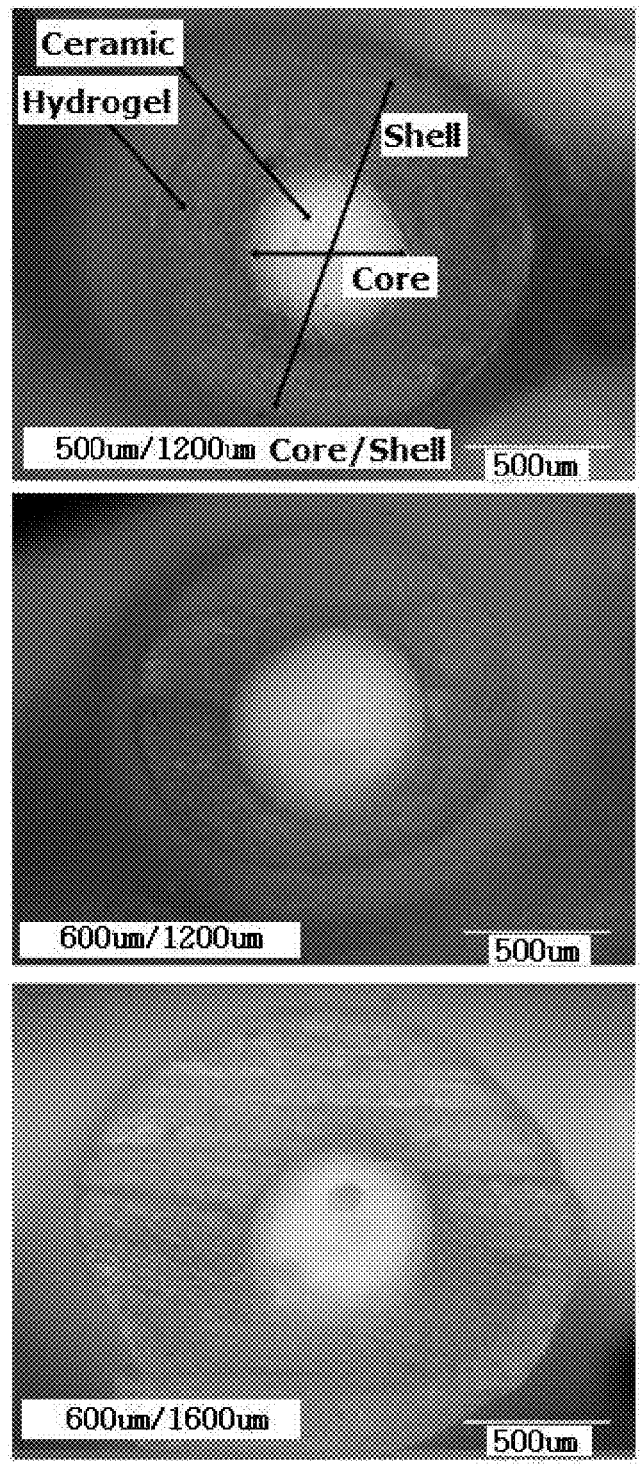

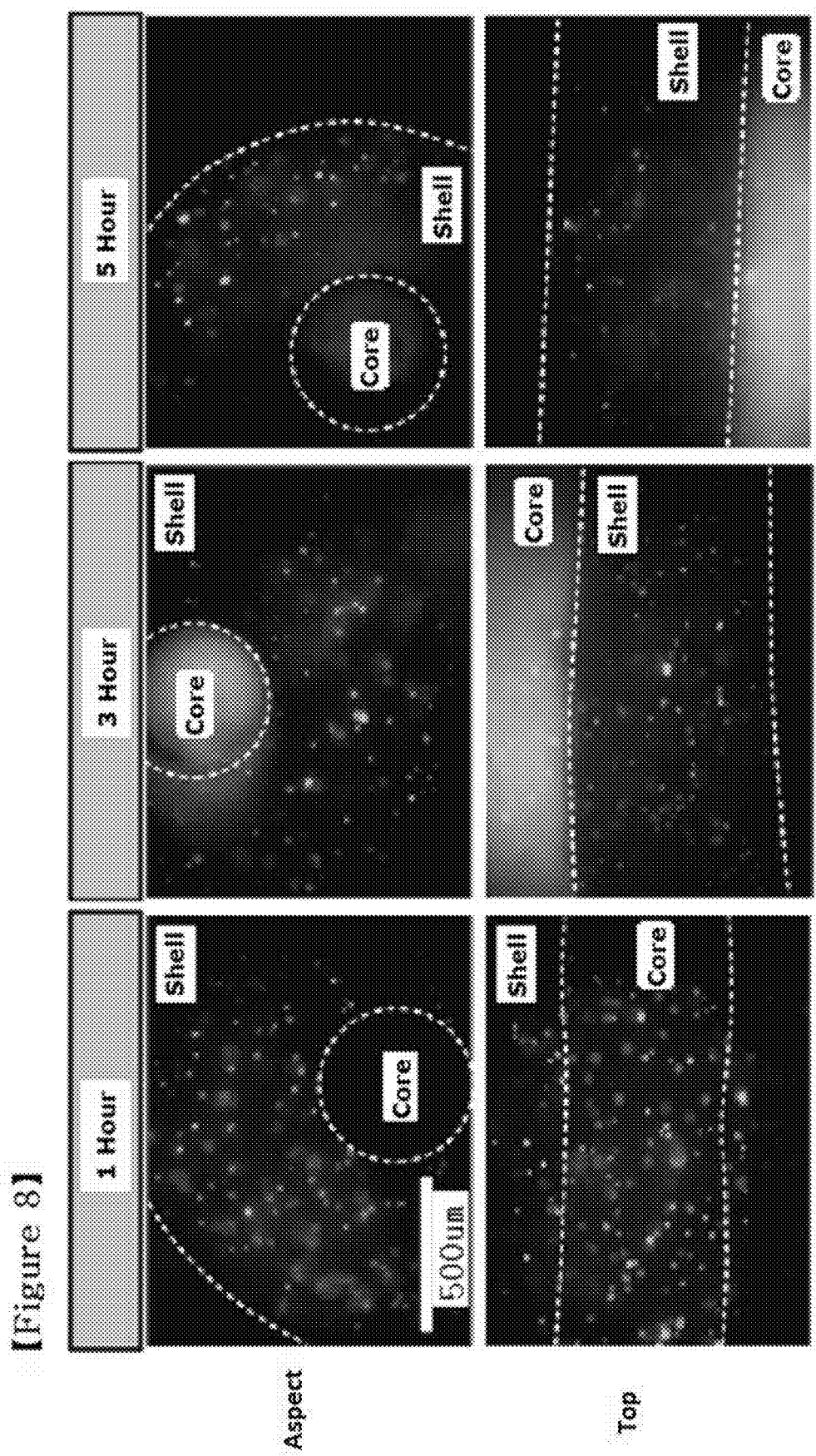
[Figure 8]

[Figure 9]
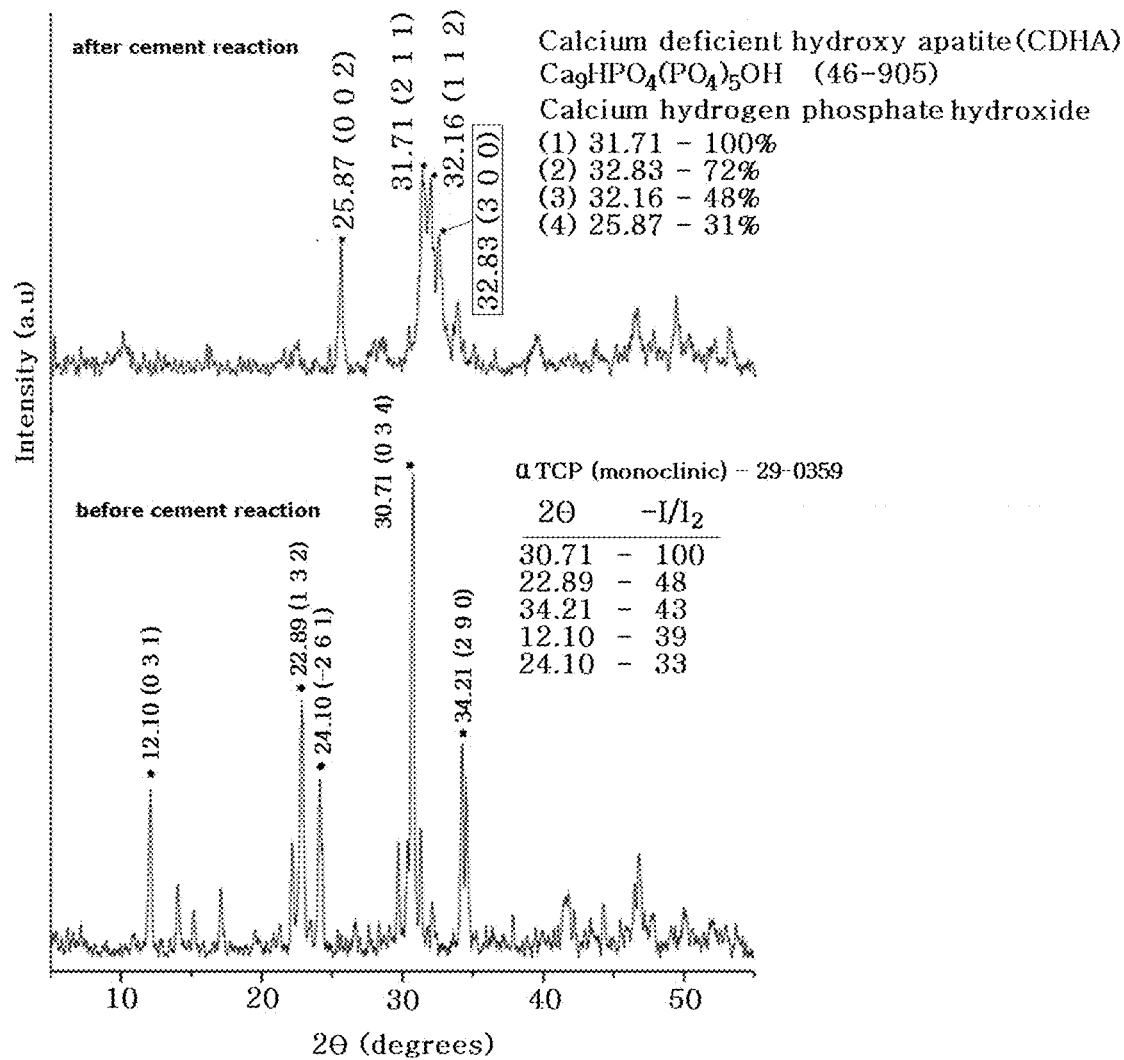

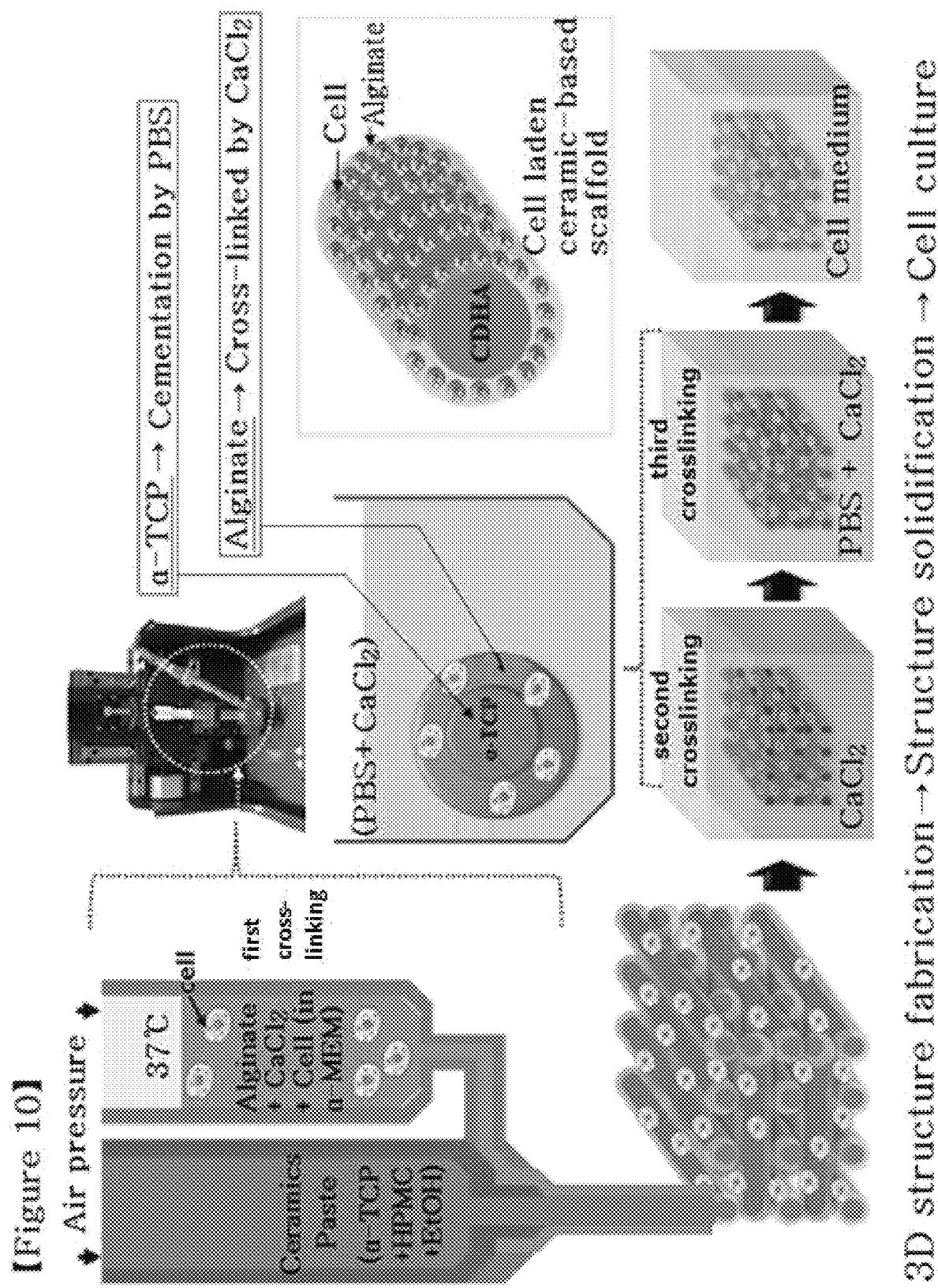

METHOD FOR MANUFACTURING SUPPORT FOR REGENERATING CORE-SHELL STRUCTURED HARD TISSUE AND SUPPORT FOR REGENERATING CORE-SHELL STRUCTURED HARD TISSUE MANUFACTURED THEREBY

This application is a Continuation of PCT/KR2014/002205 which is hereby incorporated by reference in its entirety.

TECHNICAL FIELD

The present disclosure relates to a method for manufacturing a support for regenerating core-shell structured hard tissue and the support for regenerating core-shell structured hard tissue by the method, in which a biofunctional material such as a cell can be further included in the core-shell structure.

BACKGROUND ART

Tissue engineering, which aims at restoring body functions lost due to accidents, diseases, senescence, etc., by regeneration, instead of the conventional concept of replacement, is a multi-disciplinary technical field established by the combination of various fields such as biosciences and engineering.

In a support, which is one of the three major factors constituting tissue engineering, the selection of constituting components and structure control technology are very important. That is, the support plays a role as a bridge to link between tissues for the regeneration of lost tissues through a self-restoring function, and for this, the support must have an excellent cytotropism. Additionally, the support should have a pore structure which is 3-dimensionally well connected within a constant range of size so that cells can grow well 3-dimensionally and nutrients and excrement can be well exchanged, a biodegradability so that the support can be decomposed and eliminated according to the regeneration speed, a mechanical strength so that the shape of the support can be maintained during regeneration, and excellent biostability.

In particular, it is important to secure mechanical properties according to the regeneration area in the regeneration of hard tissues such as bones and teeth. Among the functions required for the support, 3-dimensional pore structure and mechanical property can be controlled by the design and manufacturing technology of the support, whereas the remaining properties such as biodegradability, biocompatibility, and mechanical property can be mainly controlled by selection of appropriate materials and synthesis technology.

Meanwhile, in the regeneration of the hard tissues such as bones and teeth, Korean Patent Nos. 0751504 and 0941374 disclose rapid manufacturing technology which can precisely control external shapes and pore structures via computer control, for efficient manufacture of the support for performing the regeneration. The rapid manufacturing technology, for the manufacture of a support using the paste extruding deposition among them, it is important to utilize paste materials under manufacturable conditions, and for this, organic/inorganic complex materials based on a polymer material or polymer such as polycaprolactone is mostly used as a raw material (*Chemistry of Materials*, 19, 29, 6363-6366, 2007). However, among the hard tissues, about 70% of bones are ceramic-based organic/inorganic complexes consisting of inorganic materials (ceramics) represented by hydroxycarbonate apatite, and for the manufacture of the support by mimicking the biocompatibility, biodegradability, and mechanical properties of bones, it is required to manufacture a support having components similar to those of bones.

However, for the manufacture of the ceramic-based support by the rapid manufacturing technology, there is a technical limitation. That is, for the manufacture of a 3-dimensional shape in the case of ceramics, ceramic powder and an organic bindner are combined to manufacture a shape, and the organic material is controlled by high temperature sintering, and bindings between ceramic powder particles are formed to thereby obtain a mechanically stable organic material (Chemical Communication, 2139-2141, 2007), or a 3-dimensional shape is formed using polymers, a complex between ceramic powder and an organic binder based on the 3-dimensional shape, and subjected to high temperature sintering to thereby remove polymers and the organic binder (*Journal of Materials Science: Mater Med*, 18, 1071-1077, 2007). As such, in the manufacture of the conventional ceramic complexes, it is essentially to go through with a heat treatment process of high temperature sintering, and this causes large limitations on the manufacture of the organic/inorganic complex support or on the functionalization of the support into a protein, a drug, a cell, etc. Accordingly, a process which does not require a heat treatment process was developed by applying the principle of the cement reaction of ceramic powder.

In this regard, Korean Patent Application Publication No. 10-2010-0013016 discloses a process not requiring a heat treatment process by applying the principle of a cement reaction of ceramic powder, and specifically, a process, in which a paste prepared by mixing magnesium phosphate powder with a low concentration of an organic binder with excellent biostability is subjected to layer manufacturing via a rapid manufacturing process to prepare a 3-dimensional formed body, and cured by depositing in a cement solution. Accordingly, the support prepared therefrom can control the conditions of shape and structure of pores of the support, have excellent biocompatibility, and exhibit excellent mechanical strength without going through with a sintering process. In particular, unlike the conventional process of manufacturing ceramic supports, the sintering process can be replaced with the cement reaction and thus various biofunctional materials can be added thereto thereby rendering the ability of drug delivery on the supports.

Meanwhile, reviewing the case of manufacturing the support by directly adding the biofunctional material reported recently, Korean Patent Application Publication No. 10-2004-0070346 discloses a reinforced, laminated, and impregnated material analogous to the complex, as a structure of a crosslinked polyvinyl alcohol hydrogel. In detail, it relates to a material having a reinforced, laminated, impregnated, and complex properties, as a crosslinked polyvinyl alcohol hydrogel structure in the form of a bulk ((non-cellular)) or cellular)) matrix shape.

Additionally, Korean Patent No. 10-1219646 discloses a method of preparing a porous 3-dimensional support using agarose, and a porous 3-dimensional support prepared by the method. In detail, the patent relates to a method of manufacturing a porous 3-dimensional support, which includes preparing agarose, which is a material for pore-inducing material; hydrogelation of the agarose into a liquid state to prepare an agarose gel; injecting the agarose gel into a molding frame along with major raw materials of the biomaterials to be subjected to a compression molding; rapidly freezing the formed material; lyophilizing and then fixing with ethanol; and immersing in water at 50° C. or higher to remove agarose, thereby manufacturing a 3-dimensional support, in which porosity and air permeability were formed.

However, the 3-dimensional structure has problems in that the structure has an unstable mechanical property due to the ununiform mixing and distribution within the hydrogel or polymer and low in vivo activity.

Additionally, in the case of seeding and culturing cells after the manufacture of the 3-dimensional structure, it is difficult to uniformly distribute the cells for tissue regeneration over the entire 3-dimensional structure, and accordingly, there is a high risk of occurrence of side effects. That is, it is difficult to distribute the cells from the exterior of the 3-dimensional structure, which directly contacts with cells, to the interior of the structure via proliferation and growth, and even if the cells are attached, the nutrients or excrement cannot be exchanged because the pore structure is blocked due to high external density thereby causing symptoms such as necrosis.

Under these circumstances, the present inventors have studied the method of manufacturing the support for regeneration of hard tissue that can resolve the above problems, and as a result, have succeeded in manufacturing a support with a 3-dimensional structure by a layer manufacturing process, which includes injecting a paste containing a hydrogel, capable of containing a cell or biofunctional material, and a ceramic into an extrusion container including a double nozzle, and extruding the same by the layer manufacturing process, and developed a method of manufacturing a support for regenerating core-shell structured hard tissue, thereby completing the present invention.

DISCLOSURE OF THE INVENTION

Technical Problem

One object of the present invention is to provide a method for manufacturing a support for regenerating core-shell structured hard tissue.

Another object of the present invention is to provide a support for regenerating core-shell structured hard tissue.

Technical Solution

In order to achieve the objects, the present invention provides a method for manufacturing a support for regenerating core-shell structured hard tissue, including:
preparing a first paste containing a calcium phosphate ceramic (Step 1);
preparing a second paste containing hydrogel (Step 2);
adding the first paste prepared in Step 1 into a container, which is connected to an internal pipe of an extrusion container including a double nozzle, and adding the second paste prepared in Step 2 into a container, which is connected to an external pipe of the extrusion container including a double nozzle and extruding and forming by layer manufacturing process, thereby obtaining a formed body (step 3); and
immersing the formed body obtained in step 3 into a setting solution and inducing a cement reaction of the ceramic (step 4).

Additionally, the present invention provides a method for manufacturing a support for regenerating core-shell structured hard tissue, including:
preparing a first paste containing a calcium phosphate ceramic (Step 1);
preparing a second paste containing hydrogel (Step 2);
adding the second paste prepared in Step 2 into a container, which is connected to an internal pipe of an extrusion container including a double nozzle, and adding the first paste prepared in Step 1 into a container, which is connected to an external pipe of the extrusion container including a double nozzle and extruding and forming by a layer manufacturing process, thereby obtaining a formed body (step 3); and
immersing the formed body obtained in step 3 into a setting solution and inducing a cement reaction of the ceramic (step 4).

Furthermore, the present invention provides supports for regenerating core-shell structured hard tissue prepared by the methods described above.

Advantageous Effects

The method for manufacturing a support for regenerating core-shell structured hard tissue according to the present invention has an effect of manufacturing a support for regenerating core-shell structured hard tissue by a method by which a 3-dimensional structure is prepared by a layer manufacturing process through an extrusion container having a double nozzle. In addition, the support can be manufactured at room temperature, thereby having an effect of containing cells or various bio-functional materials. Furthermore, the support for regenerating core-shell structured hard tissue has a similar constitution to a bone component and thus has higher mechanical properties, and has an effect in which the cells or various bio-functional materials are uniformly distributed throughout the entire 3-dimensional structure.

BRIEF DESCRIPTION OF THE DRAWINGS

FIG. 1 shows a schematic diagram illustrating an extrusion container having a double nozzle according to the present invention;

FIG. 2 shows stereoscopic images of supports for regenerating core-shell structured hard tissue prepared in Examples 1 and 2 according to the present invention;

FIG. 3 shows stereoscopic images of supports for regenerating core-shell structured hard tissue prepared in Examples 1 and 3 according to the present invention;

FIG. 4 shows stereoscopic images of supports for regenerating core-shell structured hard tissue prepared in Examples 1 and 4 according to the present invention;

FIG. 5 shows a graph of X-ray diffraction analysis (XRD) of a support for regenerating core-shell structured hard tissue prepared in Example 1 according to the present invention;

FIG. 6 shows stereoscopic images of supports for regenerating core-shell structured hard tissue prepared in Examples 1 and 5 according to the present invention;

FIG. 7 shows cross-section images of the columns of supports for regenerating core-shell structured hard tissue prepared in Example 6 according to the present invention;

FIG. 8 shows images of vitality of cells loaded in the support for regenerating core-shell structured hard tissue prepared in Example 6 according to the present invention according to time;

FIG. 9 shows a graph of X-ray diffraction analysis (XRD) of a support for regenerating core-shell structured hard tissue prepared in Example 6 according to the present invention; and FIG. 10 shows a schematic diagram illustrating the support prepared in Example 6 according to the present invention.

MODE FOR CARRYING OUT THE INVENTION

Hereinafter, the present invention will be described in details.

The present invention provides a method for manufacturing a support for regenerating core-shell structured hard tissue, including:

preparing a first paste containing a calcium phosphate ceramic (Step 1);

preparing a second paste containing hydrogel (Step 2);

adding the first paste prepared in Step 1 into a container, which is connected to an internal pipe of an extrusion container including a double nozzle, and adding the second paste prepared in Step 2 into a container, which is connected to an external pipe of the extrusion container including a double nozzle and extruding and forming by layer manufacturing process, thereby obtaining a formed body (step 3); and immersing the formed body obtained in step 3 into a setting solution and inducing a cement reaction of the ceramic (step 4).

Hereinbelow, the method for manufacturing a support for regenerating core-shell structured hard tissue according to the present invention will be described in detail with respect to each step.

In the method for manufacturing a support for regenerating core-shell structured hard tissue according to the present invention, Step 1 is a step for preparing the first paste containing a calcium phosphate ceramic.

Step 1 is a step for preparing a paste that can be used for the layer manufacturing process, and the paste can be formed by mixing a calcium phosphate ceramic, a solvent, a thickener, etc.

In particular, the first paste to be used in Step 1 may include bioceramic that can induce a cement reaction, e.g., bioactive glass, etc., in addition to the calcium phosphate ceramic, however, any bioceramic material that can induce a cement reaction may be included in the first paste as described above.

Specifically, the calcium phosphate ceramic to be used in Step 1 may include hydroxyapatite, dicalcium phosphate dihydrate (DCPD), monocalcium phosphate monohydrate (MCPM), dicalcium phosphate anhydrous (DCPA), α-tricalcium phosphate (α-TCP), β-tricalcium phosphate, (β-TCP), etc., and preferably, α-TCP. In an exemplary embodiment, as illustrated in Reaction Scheme 1 below, α-TCP can induce a cement reaction by reacting with water into a Ca-deficient hydroxyapatiter (CDHA), and thus α-TCP may be more advantageous over β-TCP, which requires the condition of an acidic solution, in the introduction of a biofunctional material such as cells for curing purpose.

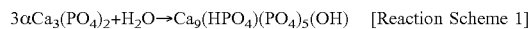

$3\alpha Ca_3(PO_4)_2 + H_2O \rightarrow Ca_9(HPO_4)(PO_4)_5(OH)$ [Reaction Scheme 1]

Additionally, the first paste of Step 1 may contain a solvent, a thickener, etc., and the solvent is preferably distilled water and a $C_1$ to $C_4$ alcohol.

Furthermore, for the thickener, an organic material with excellent biocompatibility by providing mobility and moldability on ceramic powder may be used. For example, examples of the thickener may include hydroxypropyl methylcellulose, gelatin, collagen, alginate, a chitosan solution, etc.

In particular, the content of the thickener in the first paste of Step 1 may be in the amount of 0.1 parts by weight to 20 parts by weight relative to 100 parts by weight of ceramic powder. When the content of the thickener is less than 0.1 parts by weight it will result in insufficient mobility thus making the molding difficult, whereas when the content of the thickener exceeds 20 parts by weight it may result in significant decrease in mechanical properties.

Then, in the method for manufacturing a support for regenerating core-shell structured hard tissue, Step 2 is a process for preparing the second paste.

Step 2 is a process for preparing a paste that can be used for the layer manufacturing process, and the paste can be formed by mixing a hydrogel, a crosslinking agent, etc.

Specifically, the hydrogel of Step 2 may be used by mixing alginate, gelatin, collagen, fibrinogen, chitosan, agar, matrigel, starch, pectin, hydroxy ethyl cellulose, polyvinyl alcohol, polyurethane, poly(ethylene glycol), poly(propylene glycol), methyl cellulose, carboxymethylcellulose, hyaluronan, poly(vinylpyrrolidone)), a block copolymer, etc., in a solvent, but is not limited thereto.

In particular, it is necessary to control the physical property of the paste so that the paste can have a mobility suitable for extrusion and molding by adding $H_2O$, PBS, or a solvent with secured biostability that can dissolve each hydrogel in the hydrogel, and for this purpose, the hydrogel is preferably contained in an amount of 5 parts by weight to 15 parts by weight relative to 100 parts by weight of the solvent mixture. When the hydrogel concentration is lower than 5 parts by weight it will cause difficulty to maintain the shape after the extrusion of the hydrogel, whereas when the hydrogel concentration is higher than 15 parts by weight it will increase the viscosity thus making the extrusion impossible.

Additionally, the hydrogel can induce physical (ionic, stereocomplex, and thermal) and/or chemical (UV and wet-chemical) crosslinking and the physical crosslinking is advantageous but is not limited thereto.

When the second paste of Step 2 is selected to be alginate, a crosslinking process through an ioninc reaction is required, and for the ionic reaction, a crosslinking agent such as calcium chloride ($CaCl_2$), magnesium chloride ($MgCl_2$), calcium phosphate (CaP), calcium carbonate ($CaCO_2$), etc., may be included. In particular, the crosslinking agent serves to crosslink the hydrogel component and may be used within the range of having a physical property viscosity suitable for molding. Preferably, the content of the crosslinking agent may be used in an amount of 0.05 parts by weight to 1.0 part by weight relative to 100 parts by weight of the second paste, and more preferably, 0.25 parts by weight to 1.0 part by weight.

When the content of the crosslinking agent is less than 0.05 part by weight it is difficult to form a crosslinking of the hydrogel thus making it difficult to maintain the shape after the extrusion of the second paste, whereas when the content of the crosslinking agent exceeds 1 part by weight, the pH value becomes out of the neutral range and thus a biofunctional material such as a cell may be damaged.

Furthermore, the second paste of Step 2 may further contain a biofunctional material. As such, the method for manufacturing a support for regenerating core-shell structured hard tissue according to the present invention has an advantage in that the biofunctional material can be directly included in the hydrogel, and by including the biofunctional material into the hydrogel, the biofunctional material can be uniformly distributed even into the inside of the 3-dimensional structure, thereby capable of efficiently inducing tissue regeneration.

In particular, examples of the biofunctional material to be used may include a cell, a growth factor, a protein, a protein drug, an antiproliferative agent, antithrombin, an immunosuppressant, a lipid, anti-lipid, a liposome, an antiinflammatory agent, an antitumor agent, an antiplatelet agent, an angiogenic agent, an antiangiogenic agent, a vitamin, an aptamer, an antimitotic agent, a metalloproteinase inhibitor, a NO donor, estradiol, an anticaking agent, a vasoactive agent, β-blocker, an AZ-blocker, a hormone, statin, an antioxidant, a membrane stabilizer, a calcium antagonist, a retinoid, a peptide, a lipoprotein, a polypeptide, a polynucleotide encoding a polypeptide, an enzyme, a genetic material, a chemical solvent, an energy-activator, a lymphocyte inhibitor, a macrophage inhibitor, a mixture thereof, etc.

In particular, the second paste in Step 2 may further include a cell culture when the biofunctional material is a cell.

Next, in the method for manufacturing a support for regenerating core-shell structured hard tissue according to the present invention, Step 3 is a step for obtaining a formed body by adding the first paste prepared in Step 1 into a container, which is connected to an internal pipe of an extrusion container including a double nozzle, and adding the second paste prepared in Step 2 into a container, which is connected to an external pipe of the extrusion container including a double nozzle and extruding and forming by layer manufacturing process.

Conventionally, in the case of seeding and culturing cells after the manufacture of the 3-dimensional structure, it was difficult to uniformly distribute the cells for tissue regeneration over the entire 3-dimensional structure, and accordingly, there was a high risk of causing side effects. That is, it was difficult to distribute the cells from the exterior of the 3-dimensional structure, which directly contacts with cells, to the interior of the structure via proliferation and growth, and even if the cells were attached, the nutrients or excrement could not be exchanged because the pore structure was blocked due to high external density thereby causing symptoms such as necrosis.

To solve the problems, in Step 3, the first paste containing a ceramic and the second paste containing a hydrogel are added into an extrusion container in the form of a double nozzle and extruded, and a formed body is manufactured by forming via the layer manufacturing process, and the thus-manufactured support for regenerating hard tissue has advantages in that it has a constitution similar to that of a bone thus having a high mechanical property, and that a biofunctional material such as cells can be distributed over the entire 3-dimensional structure.

In particular, the extrusion container having the double nozzle, in an exemplary embodiment, can consist of two containers being connected to the internal pipe and the external pipe, as illustrated in FIG. 1. In the container connected to the internal pipe is added with a material for forming a core and extruded, whereas the container connected to the external pipe is added with a material for forming a shell and extruded, thereby forming a core-shell structure.

Specifically, in Step 3, a support for regenerating core-shell structured hard tissue consisting of a core, which contains the calcium phosphate ceramic through the extrusion container including a double nozzle, and a shell, which contains a hydrogel provided on the core surface and encompasses the core.

Additionally, the layer manufacturing process of Step 3 can control the column thickness of the support using a various size of nozzles, and formed into various shapes (column intervals, pore size, pore shape, support shape, etc.) using a computer program.

Furthermore, although the extrusion in Step 3 can be pressed via various methods, the extrusion of the first paste containing the ceramic paste requires a high pressure and thus it is preferable to use a screw pressure, whereas the extrusion of the second paste containing a hydrogel requires a precise pressure control and thus it is preferable to use a pneumatic pressure, but is not limited thereto.

Next, in the method for manufacturing a support for regenerating core-shell structured hard tissue according to the present invention, Step 4 is a step for inducing a cement reaction of a ceramic by immersing the formed body obtained in Step 3 into a setting solution.

Since a cement reaction does not occur before treating the formed body obtained in Step 3 with a setting solution, in Step 4, the support is cured through a cement reaction by immersing in a setting solution after molding by the layer manufacturing process. As such, sufficient time can be obtained for the 3-dimensional shape and control of pore structure of a support and thus the control of the structure of the support can be more easily performed.

In particular, a step of immersing into a solution, in which a crosslinking agent such as calcium chloride ($CaCl_2$), magnesium chloride ($MgCl_2$), calcium phosphate (CaP), and calcium carbonate ($CaCO_3$) is diluted, may be further included for additional crosslinking. Here, regarding the concentration of the crosslinking agent-diluted solution, it is preferable that the concentration is adjusted by adding the crosslinking agent in an amount of 2 parts by weight to 10 parts by weight, relative to 100 parts by weight of the total diluted solution. When the content of the crosslinking agent is contained less than 2 parts by weight the crosslinking process will be slowed thus making it difficult to control the structure of the support, whereas when the content of the crosslinking agent exceeds 10 parts by weight, pH value becomes out of the neutral range, thus causing a negative effect on cells.

Additionally, it can be immersed for 1 minute to 60 minutes for additional crosslinking, and preferably from 2 minutes to 20 minutes.

Specifically, in the setting solution of Step 4, $H_2O$, phosphate buffer saline (PBS), monocalcium phosphate monohydrate (MCPM), diammonium hydrogen phosphate (DAHP), $NH_4H_2PO_4$, $KH_2PO_4$, $K_2HPO_4$, and $NaH_2PO_4$ may be used alone or in combination, according to the cement composition, and it is preferable that a neutral setting solution is used not to give a negative effect on the biofunctional material such as cells which are included in the hydrogel. Meanwhile, when monocalcium phosphate monohydrate (MCPM), diammonium hydrogen phosphate (DAHP), $NH_4H_2PO_4$, $KH_2PO_4$, $K_2HPO_4$, $NaH_2PO_4$ used alone or in combination as the setting solution, the concentration of the setting solution is preferably in the range of 0.1 M to 5.0 M. When the concentration of the setting solution is less than 0.1 M it results in the increase the time for the curing reaction, whereas when the concentration of the setting solution exceeds 5.0 M, a curing process occurs too rapidly thus causing an ununiform reaction.

Additionally, in Step 4, the formed body may be immersed in a setting solution, for example for 1 hour to 24 hours thereby inducing a cement reaction, and the time for immersion may be appropriately controlled considering the core-shell structure size and reactivity of a formed body.

Furthermore, in Step 4, the formed body may be immersed in the setting solution, thereby inducing a cement reaction and simultaneously inducing and promoting the crosslinking of the hydrogel. In particular, a crosslinking agent, such as calcium chloride ($CaCl_2$), magnesium chloride ($MgCl_2$), calcium phosphate (CaP), and calcium carbonate ($CaCO_3$), may be further contained for additional crosslinking of the hydrogel.

In particular, the additional amount of the crosslinking agent to be added is preferably a low concentration so as not to generate a precipitate formed by reacting with the setting solution, and not to change the pH value of the setting solution. For example, the amount of the crosslinking agent to be additionally added into the setting solution may be in the range of from 0.005 parts by weight to 0.1 parts by weight relative to 100 parts by weight of the setting solution and crosslinking agent.

In an exemplary embodiment, regarding alginate used as the hydrogel, the bivalent cations ($Ca^{2+}$, $Ba^{2+}$, $Sr^{2+}$, etc.) is substituted with $Na^+$ ions of alginate and thereby form a crosslinking network, and among them, $Ca^{2+}$ is expected to have the highest crosslinking effect. That is, $CaCl_2$ acts as a crosslinking agent for alginate, and thus when PBS, which was used as a setting solution, is used by mixing with $CaCl_2$, the crosslinking of alginate can be additionally induced. In the present invention, after inducing the primary crosslinking by mixing a low-concentration $CaCl_2$ with alginate and performing a molding, a secondary crosslinking, in which the resultant is immersed into a solution diluted with $CaCl_2$ for the crosslinking of alginate, may be further included, and lastly, the support is deposited into a PBS solution mixed with $CaCl_2$, and a tertiary crosslinking of alginate may be simultaneously induced with a cement reaction.

In particular, when monocalcium phosphate monohydrate (MCPM) is used as the setting solution, the tertiary crosslinking of alginate may be induced simultaneously with the cement reaction because the setting solution itself contains $Ca^{2+}$.

Additionally, in the method of manufacturing a support according to the present invention, after performing Step 4, when the support, in which a cement reaction is performed, is washed and dried, or a cell is included in the hydrogel as a biofunctional material, may further include packing along with a cell culture, after washing.

In particular, the washing may be performed using distilled water, saline, PBS, etc.

Furthermore, in the method of manufacturing a support according to the present invention, all manufacturing processes may be performed at a temperature from 5° C. to 40° C. That is, unlike the conventional ceramic curing which requires heat treatment process at high temperature, heat treatment process is not performed in the method of the present invention. Furthermore, although the heat treatment process for sintering is not performed, a support with sufficient mechanical strength to be used for regenerating hard tissue may be manufactured.

Additionally, since the process is performed at a temperature from 5° C. to 40° C., a ceramic support in which a biofunctional material is directly included can be immediately manufactured.

Meanwhile, the manufacturing method of the present invention may be performed by the layer manufacturing process as described above. However, in the manufacturing method of the present invention, the support for regenerating core-shell structured hard tissue may be manufactured by a 3D printing technology in addition to the layer manufacturing process.

That is, the 3D printing technology is a technology for manufacturing a product by printing raw materials layer by layer, after continuously reconstituting a digitalized 3-dimensional product design into a 2-dimensional cross-section, and after the digital designing of the support for regenerating a hard tissue into a core-shell structure, the resultant is applied to a 3D printing device, and thereby a support for regenerating core-shell structured hard tissue can be manufactured in the same manner as in the layer manufacturing process.

Additionally, the present invention provides a method for manufacturing a support for regenerating core-shell structured hard tissue, including:

preparing a first paste containing a calcium phosphate ceramic (Step 1);

preparing a second paste containing hydrogel (Step 2);

adding the second paste prepared in Step 2 into a container, which is connected to an internal pipe of an extrusion container including a double nozzle, and adding the first paste prepared in Step 1 into a container, which is connected to an external pipe of the extrusion container including a double nozzle and extruding and forming by a layer manufacturing process, thereby obtaining a formed body (step 3); and immersing the formed body obtained in step 3 into a setting solution and inducing a cement reaction of the ceramic (step 4).

Hereinbelow, the method for manufacturing a support for regenerating core-shell structured hard tissue according to the present invention will be described in detail with respect to each step.

In the method for manufacturing a support for regenerating core-shell structured hard tissue according to the present invention, Step 1 is a step for preparing the first paste containing a calcium phosphate ceramic.

Step 1 is a step for preparing a paste that can be used for the layer manufacturing process, and the paste can be formed by mixing a calcium phosphate ceramic, a solvent, a thickener, etc.

Specifically, the calcium phosphate ceramic to be used in Step 1 may include hydroxyapatite, dicalcium phosphate dihydrate (DCPD), monocalcium phosphate monohydrate (MCPM), dicalcium phosphate anhydrous (DCPA), α-tricalcium phosphate (α-TCP), β-tricalcium phosphate, (β-TCP), etc., and preferably, α-TCP. In an exemplary embodiment, as illustrated in Reaction Scheme 1 below, α-TCP can induce a cement reaction by reacting with water into a Ca-deficient hydroxyapatiter (CDHA), and thus α-TCP may be more advantageous over β-TCP, which requires the condition of an acidic solution, in the delivery of cells or drugs for curing purpose.

Additionally, the first paste of Step 1 may contain a solvent and a thickener, and the solvent is preferably distilled water and a $C_1$ to $C_4$ alcohol.

Furthermore, for the thickener, an organic material with excellent biocompatibility by providing mobility and moldability on ceramic powder may be used. For example, examples of the thickener may include hydroxypropyl methylcellulose, gelatin, collagen, alginate, a chitosan solution, etc.

In particular, the content of the thickener in the first paste of Step 1 may be in the amount of 0.1 parts by weight to 20 parts by weight relative to 100 parts by weight of ceramic powder. When the content of the thickener is less than 0.1 parts by weight it will result in insufficient mobility thus making the molding difficult, whereas when the content of the thickener exceeds 20 parts by weight it may result in significant decrease in mechanical properties.

Then, in the method for manufacturing a support for regenerating core-shell structured hard tissue, Step 2 is a process for preparing the second paste.

Step 2 is a process for preparing a paste that can be used for the layer manufacturing process, and the paste can be formed by mixing a hydrogel, a crosslinking agent, etc.

Specifically, the hydrogel of Step 2 may by used by mixing alginate, gelatin, collagen, fibrinogen, chitosan, agar, matrigel, starch, pectin, hydroxy ethyl cellulose, polyvinyl alcohol, polyurethane, poly(ethylene glycol), poly(propylene glycol), methyl cellulose, carboxymethylcellulose, hyaluronan, poly(vinylpyrrolidone)), and a block copolymer in a solvent, but is not limited thereto.

In particular, it is necessary to control the physical property of the paste so that the paste can have a mobility suitable for extrusion and molding by adding $H_2O$, PBS, or a solvent with secured biostability that can dissolve each hydrogel in the hydrogel, and for this purpose, the hydrogel is preferably contained in an amount of 5 parts by weight to 15 parts by weight relative to 100 parts by weight of the solvent mixture. When the hydrogel concentration is lower than 5 parts by weight it will cause difficulty to maintain the shape after the extrusion of the hydrogel, whereas when the hydrogel concentration is higher than 15 parts by weight it will increase the viscosity thus making the extrusion impossible.

Additionally, the hydrogel can induce physical (ionic, stereocomplex, and thermal) and/or chemical (UV and wet-chemical) crosslinking and the physical crosslinking is advantageous but is not limited thereto.

When the second paste of Step 2 is selected to be alginate, a crosslinking process through an ioninc reaction is required, and for the ionic reaction, a crosslinking agent such as calcium chloride ($CaCl_2$), magnesium chloride ($MgCl_2$), calcium phosphate (CaP), calcium carbonate ($CaCO_2$), etc., may be included. In particular, the crosslinking agent serves to crosslink the hydrogel component and may be used within the range of having a physical property viscosity suitable for molding. Preferably, the content of the crosslinking agent may be used in an amount of 0.05 parts by weight to 1.0 part by weight relative to 100 parts by weight of the second paste, and more preferably, 0.25 parts by weight to 1.0 part by weight.

When the content of the crosslinking agent is less than 0.05 part by weight it is difficult to form a crosslinking of the hydrogel thus making it difficult to maintain the shape after the extrusion of the second paste, whereas when the content of the crosslinking agent exceeds 1 part by weight, the pH value becomes out of the neutral range and thus a biofunctional material such as a cell may be damaged.

Furthermore, the second paste of Step 2 may further contain a biofunctional material. As such, the method for manufacturing a support for regenerating core-shell structured hard tissue according to the present invention has an advantage in that the biofunctional material can be directly included in the hydrogel, and by including the biofunctional material into the hydrogel, the biofunctional material can be uniformly distributed even into the inside of the 3-dimensional structure, thereby capable of efficiently inducing tissue regeneration.

In particular, examples of the biofunctional material to be used may include a cell, a growth factor, a protein, a protein drug, an antiproliferative agent, antithrombin, an immunosuppressant, a lipid, anti-lipid, a liposome, an antiinflammatory agent, an antitumor agent, an antiplatelet agent, an angiogenic agent, an antiangiogenic agent, a vitamin, an aptamer, an antimitotic agent, a metalloproteinase inhibitor, a NO donor, estradiol, an anticaking agent, a vasoactive agent, β-blocker, an AZ-blocker, a hormone, statin, an antioxidant, a membrane stabilizer, a calcium antagonist, a retinoid, a peptide, a lipoprotein, a polypeptide, a polynucleotide encoding a polypeptide, an enzyme, a genetic material, a chemical solvent, an energy-activator, a lymphocyte inhibitor, a macrophage inhibitor, a mixture thereof, etc.

In particular, the second paste in Step 2 may further include a cell culture when the biofunctional material is a cell.

Next, in the method for manufacturing a support for regenerating core-shell structured hard tissue according to the present invention, Step 3 is a step for obtaining a formed body by adding the first paste prepared in Step 1 into a container, which is connected to an internal pipe of an extrusion container including a double nozzle, and adding the second paste prepared in Step 2 into a container, which is connected to an external pipe of the extrusion container including a double nozzle and extruding and forming by layer manufacturing process.

Conventionally, in the case of seeding and culturing cells after the manufacture of the 3-dimensional structure, it was difficult to uniformly distribute the cells for tissue regeneration over the entire 3-dimensional structure, and accordingly, there was a high risk of causing side effects. That is, it was difficult to distribute the cells from the exterior of the 3-dimensional structure, which directly contacts with cells, to the interior of the structure via proliferation and growth, and even if the cells were attached, the nutrients or excrement could not be exchanged because the pore structure was blocked due to high external density thereby causing symptoms such as necrosis.

To solve the problems, in Step 3, the first paste containing a ceramic and the second paste containing a hydrogel are added into an extrusion container in the form of a double nozzle and extruded, and a formed body is manufactured by forming via the layer manufacturing process, and the thus-manufactured support for regenerating hard tissue has advantages in that it has a constitution similar to that of a bone thus having a high mechanical property, and that a biofunctional material such as cells can be distributed over the entire 3-dimensional structure.

In particular, the extrusion container having the double nozzle, in an exemplary embodiment, can consist of two containers being connected to the internal pipe and the external pipe, as illustrated in FIG. 1. In the container connected to the internal pipe is added with a material for forming a core and extruded, whereas the container connected to the external pipe is added with a material for forming a shell and extruded, thereby forming a core-shell structure.

Specifically, in Step 3, a support for regenerating core-shell structured hard tissue consisting of a core, which contains the calcium phosphate ceramic through the extrusion container including a double nozzle, and a shell, which contains a hydrogel provided on the core surface and encompasses the core.

Additionally, the layer manufacturing process of Step 3 can control the column thickness of the support using a various size of nozzles, and formed into various shapes (column intervals, pore size, pore shape, support shape, etc.) using a computer program.

Furthermore, although the extrusion in Step 3 can be pressed via various methods, the extrusion of the first paste containing the ceramic paste requires a high pressure and thus it is preferable to use a screw pressure, whereas the extrusion of the second paste containing a hydrogel requires a precise pressure control and thus it is preferable to use a pneumatic pressure, but is not limited thereto.

Next, in the method for manufacturing a support for regenerating core-shell structured hard tissue according to the present invention, Step 4 is a step for inducing a cement reaction of a ceramic by immersing the formed body obtained in Step 3 into a setting solution.

Since a cement reaction does not occur before treating the formed body obtained in Step 3 with a setting solution, in Step 4, the support is cured through a cement reaction by immersing in a setting solution after molding by the layer manufacturing process. As such, sufficient time can be obtained for the 3-dimensional shape and control of pore structure of a support and thus the control of the structure of the support can be more easily performed.

In particular, a step of immersing into a solution, in which a crosslinking agent such as calcium chloride ($CaCl_2$), magnesium chloride ($MgCl_2$), calcium phosphate (CaP), and calcium carbonate ($CaCO_3$) is diluted, may be further included for additional crosslinking. Here, regarding the concentration of the crosslinking agent-diluted solution, it is preferable that the concentration is adjusted by adding the crosslinking agent in an amount of 2 parts by weight to 10 parts by weight, relative to 100 parts by weight of the total diluted solution. When the content of the crosslinking agent is contained less than 2 parts by weight the crosslinking process will be slowed thus making it difficult to control the structure of the support, whereas when the content of the crosslinking agent exceeds 10 parts by weight, pH value becomes out of the neutral range, thus causing a negative effect on cells.

Additionally, it can be immersed for 1 minute to 60 minutes for additional crosslinking, and preferably from 2 minutes to 20 minutes.

Specifically, in the setting solution of Step 4, $H_2O$, phosphate buffer saline (PBS), monocalcium phosphate monohydrate (MCPM), diammonium hydrogen phosphate (DAHP), $NH_4H_2PO_4$, $KH_2PO_4$, $K_2HPO_4$, and $NaH_2PO_4$ may be used alone or in combination, according to the cement composition, and it is preferable that a neutral setting solution is used not to give a negative effect on the biofunctional material such as cells which are included in the hydrogel. Meanwhile, when monocalcium phosphate monohydrate (MCPM), diammonium hydrogen phosphate (DAHP), $NH_4H_2PO_4$, $KH_2PO_4$, $K_2HPO_4$, $NaH_2PO_4$ used alone or in combination as the setting solution, the concentration of the setting solution is preferably in the range of 0.1 M to 5.0 M. When the concentration of the setting solution is less than 0.1 M it results in the increase the time for the curing reaction, whereas when the concentration of the setting solution exceeds 5.0 M, a curing process occurs too rapidly thus causing an ununiform reaction.

Additionally, in Step 4, the formed body may be immersed in a setting solution, for example for 1 hour to 24 hours thereby inducing a cement reaction, and the time for immersion may be appropriately controlled considering the core-shell structure size and reactivity of a formed body.

Furthermore, in Step 4, the formed body may be immersed in the setting solution, thereby inducing a cement reaction and simultaneously inducing and promoting the crosslinking of the hydrogel. In particular, a crosslinking agent, such as calcium chloride ($CaCl_2$), magnesium chloride ($MgCl_2$), calcium phosphate (CaP), and calcium carbonate ($CaCO_3$), may be further contained for additional crosslinking of the hydrogel.

In particular, the additional amount of the crosslinking agent to be added is preferably a low concentration so as not to generate a precipitate formed by reacting with the setting solution, and not to change the pH value of the setting solution. For example, the amount of the crosslinking agent to be additionally added into the setting solution may be in the range of from 0.005 parts by weight to 0.1 parts by weight relative to 100 parts by weight of the setting solution and crosslinking agent.

In an exemplary embodiment, regarding alginate used as the hydrogel, the bivalent cations ($Ca^{2+}$, $Ba^{2+}$, $Sr^{2+}$, etc.) is substituted with $Na^+$ ions of alginate and thereby form a crosslinking network, and among them, $Ca^{2+}$ is expected to have the highest crosslinking effect. That is, $CaCl_2$ acts as a crosslinking agent for alginate, and thus when PBS, which was used as a setting solution, is used by mixing with $CaCl_2$, the crosslinking of alginate can be additionally induced. In the present invention, after inducing the primary crosslinking by mixing a low-concentration $CaCl_2$ with alginate and performing a molding, a secondary crosslinking, in which the resultant is immersed into a solution diluted with $CaCl_2$ for the crosslinking of alginate, may be further included, and lastly, the support is deposited into a PBS solution mixed with $CaCl_2$, and a tertiary crosslinking of alginate may be simultaneously induced with a cement reaction.

In particular, when monocalcium phosphate monohydrate (MCPM) is used as the setting solution, the tertiary crosslinking of alginate may be induced simultaneously with the cement reaction because the setting solution itself contains $Ca^{2+}$.

Additionally, in the method of manufacturing a support according to the present invention, after performing Step 4, when the support, in which a cement reaction is performed, is washed and dried, or a cell is included in the hydrogel as a biofunctional material, may further include packing along with a cell culture, after washing.

In particular, the washing may be performed using distilled water, saline, PBS, etc.

Furthermore, in the method of manufacturing a support according to the present invention, all manufacturing processes may be performed at a temperature from 5° C. to 40° C. That is, unlike the conventional ceramic curing which requires heat treatment process at high temperature, heat treatment process is not performed in the method of the present invention. Furthermore, although the heat treatment process for sintering is not performed, a support with sufficient mechanical strength to be used for regenerating hard tissue may be manufactured.

Additionally, since the process is performed at a temperature from 5° C. to 40° C., a ceramic support in which a biofunctional material is directly included can be immediately manufactured.

Additionally, the present invention provides a support for regenerating core-shell structured hard tissue by the method described above.

Hereinbelow, the support for regenerating core-shell structured hard tissue according to the present invention will be described in detail.

In a support for regenerating core-shell structured hard tissue according to the present invention, the core-shell may consist of a core, which contains a calcium phosphate ceramic, and a shell, which contains a hydrogel provided on the core surface and encompasses the core, or may consist of a core, which contains a hydrogel, and a shell, which contains a calcium phosphate ceramic provided on the core surface and encompasses the core.

The support for regenerating core-shell structured hard tissue according to the present invention has advantages in that it has a constitution similar to that of a bone thus having a high mechanical property, and that a cell or a biofunctional material is distributed over the entire 3-dimensional structure.

In particular, the calcium phosphate ceramic to be used may include hydroxyapatite, dicalcium phosphate dihydrate (DCPD), monocalcium phosphate monohydrate (MCPM), dicalcium phosphate anhydrous (DCPA), α-tricalcium phosphate (α-TCP), β-Tricalcium phosphate, (β-TCP), etc., but any biocompatible ceramic material that can be used as a support for regenerating hard tissue may be used without limitation.

Additionally, the hydrogel may be used by mixing alginate, gelatin, collagen, fibrinogen, chitosan, agar, matrigel, starch, pectin, hydroxy ethyl cellulose, polyvinyl alcohol, polyurethane, poly(ethylene glycol), poly(propylene glycol), methyl cellulose, carboxymethylcellulose, hyaluronan, poly(vinylpyrrolidone)), a block copolymer, etc., in a solvent, but is not limited thereto.

In particular, it is necessary to control the physical property of the paste so that the paste can have a mobility suitable for extrusion and molding by adding $H_2O$, PBS, or a solvent with secured biostability that can dissolve each hydrogel in the hydrogel, and for this purpose, the hydrogel is preferably contained in an amount of 5 parts by weight to 15 parts by weight relative to 100 parts by weight of the solvent mixture. When the hydrogel concentration is lower than 5 parts by weight it will cause difficulty to maintain the shape after the extrusion of the hydrogel, whereas when the hydrogel concentration is higher than 15 parts by weight it will increase the viscosity thus making the extrusion impossible.

Additionally, the hydrogel can induce physical (ionic, stereocomplex, and thermal) and/or chemical (UV and wet-chemical) crosslinking and the physical crosslinking is advantageous but is not limited thereto.

When the second paste of Step 2 is selected to be alginate, a crosslinking process through an ioninc reaction is required, and for the ionic reaction, a crosslinking agent such as calcium chloride ($CaCl_2$), magnesium chloride ($MgCl_2$), calcium phosphate (CaP), calcium carbonate ($CaCO_2$), etc., may be included. In particular, the crosslinking agent serves to crosslink the hydrogel component and may be used within the range of having a physical property viscosity suitable for molding. Preferably, the content of the crosslinking agent may be used in an amount of 0.05 parts by weight to 1.0 part by weight relative to 100 parts by weight of the second paste, and more preferably, 0.25 parts by weight to 1.0 part by weight.

When the content of the crosslinking agent is less than 0.05 part by weight it is difficult to form a crosslinking of the hydrogel thus making it difficult to maintain the shape after the extrusion of the second paste, whereas when the content of the crosslinking agent exceeds 1 part by weight, the pH value becomes out of the neutral range and thus a biofunctional material such as a cell may be damaged.

Furthermore, the second paste of Step 2 may further contain a biofunctional material. As such, the method for manufacturing a support for regenerating core-shell structured hard tissue according to the present invention has an advantage in that the biofunctional material can be directly included in the hydrogel, and by including the biofunctional material into the hydrogel, the biofunctional material can be uniformly distributed even into the inside of the 3-dimensional structure, thereby capable of efficiently inducing tissue regeneration.

In particular, examples of the biofunctional material to be used may include a cell, a growth factor, a protein, a protein drug, an antiproliferative agent, antithrombin, an immunosuppressant, a lipid, anti-lipid, a liposome, an antiinflammatory agent, an antitumor agent, an antiplatelet agent, an angiogenic agent, an antiangiogenic agent, a vitamin, an aptamer, an antimitotic agent, a metalloproteinase inhibitor, a NO donor, estradiol, an anticaking agent, a vasoactive agent, β-blocker, an AZ-blocker, a hormone, statin, an antioxidant, a membrane stabilizer, a calcium antagonist, a retinoid, a peptide, a lipoprotein, a polypeptide, a polynucleotide encoding a polypeptide, an enzyme, a genetic material, a chemical solvent, an energy-activator, a lymphocyte inhibitor, a macrophage inhibitor, a mixture thereof, etc.

In particular, the second paste in Step 2 may further include a cell culture when the biofunctional material is a cell.

PREFERRED EMBODIMENTS OF THE INVENTION

Hereinafter, the present invention will be described in details with reference to the following Examples. However, these Examples are for illustrative purposes only, and the scope of the present invention is not limited to these Examples.

Example 1

Preparation 1 of a Support for Regenerating Core-Shell Structured Hard Tissue Using β-TCP Step 1: β-tricalcium phosphate (β-TCP) powder was added with ethanol and subjected to a ball-milling process, and thereby β-TCP in a size of 50 μm to 100 μm was prepared. Then, 3 g of the ball-milled β-TCP powder was uniformly mixed with a solution, in which 1% hydroxypropyl methylcellulose was dissolved in 30% ethanol, at a 2:1 powder/liquid ratio, and thereby the first paste was prepared.

Step 2: 1.5 g of sodium alginate (80 cP to 120 cP) and 0.05 g of calcium chloride ($CaCl_2$) were mixed with 20 mL of distilled water, and thereby the second paste was prepared.

Step 3: The first past prepared in Step 1 was added inside of a double nozzle extrusion container, and the second paste prepared in Step 2 was added to the outside of the double nozzle extrusion container, and a formed body with controlled shape and pore size of a support was prepared using a computer program of a self-manufactured layer manufacturing device. In particular, the support was controlled so that the size of the diameter of the support core becomes 600 μm, the pore structure of the support has a shape of a simple lattice, and the gap between columns becomes 2.5 mm, thereby preparing a formed body for regenerating core-shell structured hard tissue in a simple lattice shape with a pore size of 100 μm to 700 μm. The thus-prepared formed body was dried at room temperature for one day.

Step 4: The formed body for regenerating core-shell structured hard tissue obtained in Step 3 was immersed in 0.1 monocalcium phosphate monohydrate to induce a cement reaction of the ceramic (β-TCP) paste and the crosslinking of hydrogel (alginate), and the Brushite support, which was formed by the cement reaction, was washed with distilled water, dried at room temperature for one day, thereby preparing a support for regenerating core-shell structured hard tissue.

Example 2

Preparation 2 of a Support for Regenerating Core-Shell Structured Hard Tissue Using β-TCP A support for regenerating core-shell structured hard tissue was prepared in the same manner as in Example 1, except that the nozzle size of the double nozzle was adjusted to 800 μm in Step 3 of Example 1.

Example 3

Preparation 3 of a Support for Regenerating Core-Shell Structured Hard Tissue Using β-TCP A support for regenerating core-shell structured hard tissue was prepared in the same manner as in Example 1, except that the gap between columns of the support was adjusted to 3.0 mm using a computer program in Step 3 of Example 1.

Example 4

Preparation 4 of a Support for Regenerating Core-Shell Structured Hard Tissue Using β-TCP A support for regenerating core-shell structured hard tissue was prepared in the same manner as in Example 1, except that the support was prepared in the shape of a zigzag using a computer program in Step 3 of Example 1.

Example 5

Preparation 5 of a Support for Regenerating Core-Shell Structured Hard Tissue Using β-TCP A support for regenerating core-shell structured hard tissue was prepared in the same manner as in Example 1, except that the support was prepared by adding the second paste into the inside of the double nozzle extrusion container while adding the first paste to the outside of the double nozzle extrusion container in Step 3 of Example 1.

Example 6

Preparation 1 of a Support for Regenerating Core-Shell Structured Hard Tissue Using α-TCP The preparation process of Example 6 is shown in FIG. 10.

Step 1: α-tricalcium phosphate (α-TCP) powder was added with ethanol and subjected to a ball-milling process, and thereby α-TCP in a size of 50 μm to 100 μm was prepared. Then, 2 g of the ball-milled α-TCP powder was uniformly mixed with a solution, in which 1% hydroxypropyl methylcellulose was dissolved in 30% ethanol, at a 2:1 powder/liquid ratio, and thereby the first paste was prepared.

Step 2: 12.5 wt % of sodium alginate (80 cP to 120 cP) was mixed by adding into phosphate buffered saline (PBS). The mixed alginate solution was added with 0.5 wt % $CaCl_2$ and mixed at 37° C. for 10 minutes so that the first crosslinking can occur uniformly.

Then, the mixture was added with 1 mL of α-minimum essential medium (α-MEM), which is a cell culture, and mixed uniformly. While maintaining the mixture at 37° C., MC3T3-E1 cells ($1 \times 10^5$/mL), which were isolated from cranial tissue of young fetus of a C57BL16 mouse, were added into alginate paste and carefully mixed not to damage the cells and thereby the second paste was prepared.

Step 3: The first past prepared in Step 1 was added inside of a double nozzle extrusion container, and the second paste prepared in Step 2 was added to the outside of the double nozzle extrusion container, and a formed body with controlled shape and pore size of a support was prepared using a computer program of a self-manufactured layer manufacturing device. In particular, the support was controlled so that the size of the diameter of the support core becomes 600 μm, the shell diameter becomes 1200 μm, the pore structure of the support has a shape of a simple lattice, and the gap between columns becomes 2.5 mm, thereby preparing a formed body for regenerating core-shell structured hard tissue in a simple lattice shape with a pore size of 100 μm to 700 μm.

Step 4: The formed body obtained in Step 3 was cross-linked by immersing in a 2.5 wt % $CaCl_2$ solution for 2 minutes to 20 minutes, and washed with PBS to remove unnecessary $CaCl_2$.

Additionally, to increase cell viability using a ceramic setting solution, the formed boy was immersed in PBS solution instead of water for 6 hours, and induced the cement reaction of α-TCP with CDHA thereby stabilizing the structure. In particular, to rectify the crosslinking of the hydrogel, the PBS solution was further added with 0.01 wt % $CaCl_2$.

Example 7

Preparation 2 of a Support for Regenerating Core-Shell Structured Hard Tissue Using α-TCP A support was prepared in the same manner, except that the diameter of the support core was adjusted to 600 μm and the shell diameter to 1200 μm in Step 3 of Example 6.

Example 8

Preparation 3 of a Support for Regenerating Core-Shell Structured Hard Tissue Using α-TCP A support was prepared in the same manner, except that the diameter of the support core was adjusted to 600 μm and the shell diameter to 1600 μm in Step 3 of Example 6.

Example 9

Preparation 4 of a Support for Regenerating Core-Shell Structured Hard Tissue Using α-TCP A support for regenerating core-shell structured hard tissue was prepared in the same manner as in Example 1, except that the support was prepared by adding the second paste into the inside of the double nozzle extrusion container while adding the first paste to the outside of the double nozzle extrusion container in Step 3 of Example 6.

Experimental Example 1

Stereomicroscopic Observation of a Support for Regenerating Core-Shell Structured Hard Tissue Prepared Using β-TCP In order to confirm the surface shape of the support for regenerating core-shell structured hard tissue according to the present invention, the supports for regenerating core-shell structured hard tissue prepared in Examples 1 to 4 were observed under a stereomicroscope, and the results are shown in FIGS. 2 to 4 and FIG. 6.

As illustrated in FIG. 2, Example 1 and Example 2, which relate to the support for regenerating core-shell structured hard tissue, show the mutual difference in the diameter of the core.

Additionally, as illustrated in FIG. 3, when comparing Example 1 and Example 3, it was confirmed that the gap between the columns can be adjusted. Additionally, as illustrated in FIG. 4, when comparing Example 1 and Example 4, it was confirmed they have mutually different pore structures of a rectangular simple lattice structure and a zigzag structure.

Furthermore, as illustrate in FIG. 6, it was confirmed that when ceramic was used as the core or ceramic was used as the shell, both cases could prepare a core-shell structure.

Experimental Example 2

X-Ray Diffraction Analysis of a Support for Regenerating Core-Shell Structured Hard Tissue Prepared Using β-TCP In order to observe the changes in phase according to the progress of the cement reaction of the β-TCP paste in a support for regenerating core-shell structured hard tissue according to the present invention, the support for regenerating core-shell structured hard tissue prepared in Example 1 was analyzed (36 kV, 26 mA, and 5°/min) using the X-ray diffraction analysis (XRD), and the results are shown in FIG. 5.

As illustrated in FIG. 5, it was confirmed that Brushite peak was formed through the graph of the X-ray diffraction analysis according to the time progressed of the cement reaction of the β-TCP used in preparing the support for regenerating core-shell structured hard tissue, which was prepared in Example 1. Within 1.5 hours after the deposition in the MCPM solution, a weak Brushite peak started to from, and in 3 hours, the peak of (020) surface, which is the main peak, started to become strong, and in 6 hours, all the peaks at 11.6° (020), 20.9° (021), 29.2° (041), 30.5° (−221), and 34.1° (−220) were explicitly detected. These peaks can be more strongly detected 24 hours after the deposition, and some peaks (27.7°, 31°, and 34.3°) corresponding to β-TCP, which is a part of raw materials, are detected, but it was confirmed that most were substituted with Brushite by the cement reaction.

Experimental Example 3

Stereomicroscopic Observation of a Support for Regenerating Core-Shell Structured Hard Tissue Prepared Using α-TCP In order to confirm the cross-section of the columns of the support for regenerating core-shell structured hard tissue according to the present invention, the supports for regenerating core-shell structured hard tissue prepared in Examples 6 to 8 were observed under a stereomicroscope, and the results are shown in FIG. 7.

As illustrated in FIG. 7, it can be seen that the supports for regenerating core-shell structured hard tissue prepared in Examples 6 to 8 had mutually different diameters of the cores and the shells.

Accordingly, the support for regenerating core-shell structured hard tissue can be prepared to have a desired diameter.

Experimental Example 4

Evaluation of Cell Viability within a Support Along with Time

In order to confirm the cell viability according to the time within the support for regenerating core-shell structured hard tissue, the support for regenerating core-shell structured hard tissue was prepared in Example 6, and the upper side and the cross-section were observed under a stereomicroscope. The results are shown in FIG. 8.

As illustrated in FIG. 8, the observation of the upper side appears to show that cells are distributed over the entire support but it can be seen that cells are distributed on the shell consisting of hydrogel. One hour after the printing, dead cells (red) were hardly observed, and after 5 hours of progress, some dead cells (red) were observed but most cells were shown to survive (green).

Accordingly, the support for regenerating core-shell structured hard tissue according to the present invention enables the preparation of a ceramic-based support and a cell printing concurrently, and since the cell viability can be confirmed even after the preparation of the support, the support can significantly improve the role of the support for regenerating hard tissue which 3-dimensionally induces the tissue regeneration.

Experimental Example 5

X-Ray Diffraction Analysis of a Support for Regenerating Core-Shell Structured Hard Tissue Prepared Using α-TCP In order to observe the formation of Ca-deficient hydroxyl apatiter (CDHA) according to the progress of the cement reaction of α-TCP paste in the support for regenerating core-shell structured hard tissue according to the present invention, the support for regenerating core-shell structured hard tissue prepared in Example 6 was analyzed (36 kV, 26 mA, and 5°/min) using the X-ray diffraction analysis (XRD), and the results are shown in FIG. 9.

As illustrated in FIG. 9, as a result of the cement reaction of the α-TCP paste used in the preparation of the support for regenerating core-shell structured hard tissue prepared in Example 6, it was confirmed by X-ray diffraction analysis (XRD) that Ca-deficient hydroxy apatiter (CDHA) was formed.

Specifically, the unique peaks of α-TCP (12.10°, 22.89°, 24.10°, 30.71°, and 34.21°) were observed before the cement reaction, and also all the unique peaks of Ca-deficient hydroxy apatiter (CDHA) (25.87°, 31.71°, 32.16°, and 32.83°) are explicitly observed after the cement reaction, it was confirmed that most α-TCP was progressed to CDHA by the cement reaction.

Accordingly, the support for regenerating core-shell structured hard tissue according to the present invention can cure a ceramic by a cement reaction without heat treatment at high temperature, and thus it can be used as a support for regenerating hard tissue.

INDUSTRIAL APPLICABILITY

The method for manufacturing a support for regenerating core-shell structured hard tissue according to the present invention has an effect of manufacturing a support for regenerating core-shell structured hard tissue by a method by which a 3-dimensional structure is prepared by a layer manufacturing process through an extrusion container having a double nozzle. In addition, the support can be manufactured at room temperature, thereby having an effect of containing cells or various bio-functional materials. Furthermore, the support for regenerating core-shell structured hard tissue has a similar constitution to a bone component and thus has higher mechanical properties, and has an effect in which the cells or various bio-functional materials are uniformly distributed throughout the entire 3-dimensional structure.

The invention claimed is:

1. A support for regenerating core-shell structured hard tissue, said support comprising a hydrogel, cells and a calcium phosphate ceramic, wherein:
the support is configured as a layered structure of columns;
each of the columns comprises a core and a shell;
the core comprises the calcium phosphate ceramic;
the core is free of the hydrogel and the cells;
the shell consisting essentially of the hydrogel and the cells; the hydrogel consists essentially of alginate; and
the shell is free of the calcium phosphate ceramic, is provided on the surface of the core and encompasses the core;
wherein the columns are manufactured by a method comprising the following steps:
preparing a first paste comprising the calcium phosphate ceramic (Step 1);
preparing a second paste consisting essentially of the hydrogel and the cells (Step 2);
forming the core by adding the first paste prepared in Step 1 into an internal pipe of an extrusion container having a double nozzle, and forming the shell by adding the second paste prepared in Step 2 into an external pipe of the extrusion container having a double nozzle and extruding and forming by layer manufacturing process, thereby obtaining a formed body (step 3) comprising the core and shell;
and immersing the formed body obtained in step 3 into a setting solution and inducing a cement reaction of the ceramic (step 4),
wherein the hydrogel comprises at least one cross-linking agent selected from the group consisting of $CaCl_2$, $MgCl_2$, CaP and $CaCO_2$ in an amount of 0.05 parts by weight to 1.0 part by weight relative to 100 parts by weight of the second paste, and
wherein the second paste comprises the hydrogel in an amount of 5 parts by weight to 15 parts by weight relative to 100 parts by weight of the second paste.

2. The support of claim 1, wherein the calcium phosphate ceramic is at least one member selected from the group consisting of hydroxyapatite, dicalcium phosphate dihydrate (DCPD), monocalcium phosphate monohydrate (MCPM), dicalcium phosphate anhydrous (DCPA), α-tricalcium phosphate (α-TCP), and β-tricalcium phosphate (β-TCP).

3. The support of claim 1, wherein the calcium phosphate ceramic is α-tricalcium phosphate (α-TCP).

4. The support of claim 1, wherein the calcium phosphate ceramic is cured by a setting solution, in which the setting solution is at least one member selected from the group consisting of $H_2O$, phosphate buffer saline (PBS), monocalcium phosphate monohydrate (MCPM), diammonium hydrogen phosphate (DAHP), $NH_4H_2PO_4$, $KH_2PO_4$, $K_2HPO_4$, and $NaH_2PO_4$.

5. The support of claim 4, wherein the setting solution further comprises at least one crosslinking agent selected from the group consisting of calcium chloride ($CaCl_2$), magnesium chloride ($MgCl_2$), calcium phosphate (CaP), and calcium carbonate ($CaCO_3$) for additional crosslinking.

* * * * *